United States Patent [19]

Lee et al.

[11] Patent Number: 5,317,099
[45] Date of Patent: May 31, 1994

[54] PROCESS FOR THE PREPARATION OF CEPHEM DERIVATIVES

[75] Inventors: Kwang H. Lee, Kwacheon; Dong H. Ko, Kyonggi-do; Young J. Kim; Myung X. Xiang, both of Seoul; Myeong S. Yoon, Kyonggi-do, all of Rep. of Korea

[73] Assignee: Cheil Foods & Chemicals, Inc., Seoul, Rep. of Korea

[21] Appl. No.: 959,359

[22] Filed: Oct. 13, 1992

[30] Foreign Application Priority Data

Nov. 18, 1991 [KR] Rep. of Korea ............... 91-20505

[51] Int. Cl.$^5$ ........................................... C07D 501/06
[52] U.S. Cl. ..................................... 540/222; 540/227; 540/228; 540/230
[58] Field of Search ............. 540/222, 221, 227, 228

[56] References Cited

U.S. PATENT DOCUMENTS

| | | | |
|---|---|---|---|
| 4,152,432 | 5/1979 | Heymes et al. | 424/246 |
| 4,166,115 | 8/1979 | Takaya et al. | 424/246 |
| 4,196,205 | 4/1980 | Heymes et al. | 424/246 |
| 4,278,671 | 7/1981 | Ochiai et al. | 424/246 |
| 4,279,818 | 7/1981 | Takaya et al. | 424/246 |
| 4,283,396 | 8/1981 | Heymes et al. | 424/246 |
| 4,304,770 | 12/1981 | Takaya et al. | 424/246 |
| 4,316,019 | 2/1982 | Takaya et al. | 424/246 |
| 4,327,210 | 4/1982 | Montavon et al. | 544/27 |
| 4,331,664 | 5/1982 | Takaya et al. | 424/246 |
| 4,370,326 | 1/1983 | Takaya et al. | 424/246 |
| 5,128,465 | 7/1992 | Kamiya et al. | 540/222 |
| 5,159,070 | 10/1992 | Heymes et al. | 540/222 |

FOREIGN PATENT DOCUMENTS

| | | |
|---|---|---|
| 1106358 | 8/1981 | Canada. |
| 0037380 | 7/1981 | European Pat. Off. |
| 0175814 | 2/1986 | European Pat. Off. |
| 2025933A | 1/1980 | United Kingdom. |

OTHER PUBLICATIONS

Fujisawa et al., "Simple and Chemoselective Synthesis of Ketones from Carboxylic Acids and Grignard Reagents Using Dichlorotriphenylphosphorane," *Chem. Letters*, 1983, pp. 1267-1270.

*Primary Examiner*—Nicholas S. Rizzo
*Attorney, Agent, or Firm*—Burns, Doane, Swecker & Mathis

[57] ABSTRACT

A process for preparing B-lactam derivatives of the formula (I):

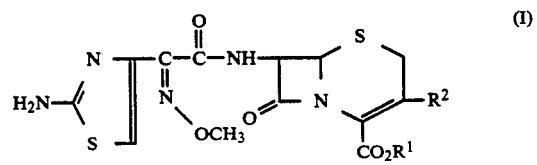

wherein $R^1$ represents hydrogen or a metal salt; and $R^2$ represents hydrogen, acetoxy methyl, (2,5-dihydro-2-methyl-6-hydroxy-5-oxo-as-triazin-3-yl)thiomethyl or (1-methyl-1-H-tetrazol-5-yl)thiomethyl is disclosed. This process comprises the steps of (a) reacting triphenylphosphine and hexachloroethane or carbon tetrachloride with 2-(2-aminothiazol-4-yl)-2-syn-methoxyimino acetic acid in an organic solvent to give the corresponding acyloxyphosphonium chloride derivative of the formula:

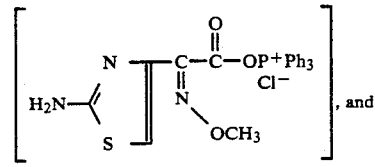

, and (b) acylating a previously silylated derivative of 7-ACA with this acyloxyphosphonium chloride derivative without its isolation.

6 Claims, No Drawings

PROCESS FOR THE PREPARATION OF CEPHEM DERIVATIVES

BACKGROUND OF THE INVENTION

1. Field of the Invention

The present invention relates to a novel process for preparing β-lactam derivatives, which are useful antibiotics, having the formula (I):

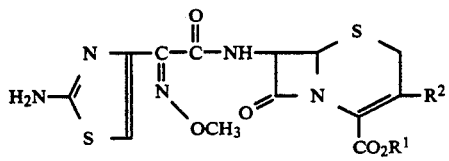

wherein $R^1$ represents hydrogen or a metal salt; and $R^2$ represents hydrogen, acetoxy methyl, (2,5-dihydro-2-methyl-6-hydroxy-5-oxo-as-triazin-3-yl)thiomethyl or (1-methyl-1H-tetrazol-5-yl)thiomethyl.

2. Description of the Prior Art

Hitherto, a number of processes for the preparation of semi-synthesized β-lactam antibiotic materials have been proposed.

For instance, it is well known that an acylated compound of the formula (I) above can be prepared by converting an amino-protected organic acid of the formula (II):

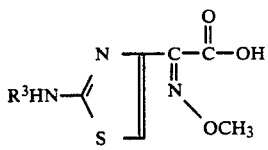

wherein $R^3$ is an amino-protecting group, into its activated derivatives, and then by acylating 7-ADCA (7-aminodesacetoxycephalosporanic acid), 7-ACA (7-aminocephalosporanic acid) or its derivatives with the activated derivatives.

The activated derivatives of the compound of the formula (II) may include an acid chloride, an acid anhydride, an activated ester, an activated amide, an activated amide solvate, and so forth.

In order to use an acid chloride as the activated derivative, the organic acid (II) is reacted with thionyl chloride ($SOCl_2$), phosphorous trichloride ($PCl_3$), phosphorous pentachloride ($PCl_5$), or phosphorous oxychloride ($POCl_3$). The resulting acid chloride is acylated with 7-ADCA, 7-ACA or its derivatives followed by removing the protecting $R^3$ group to give a compound of the formula (I): see Japanese Laid-Open (Kokai) Patent Publication Nos. 52-102,096; 53-34,795; 53-68,796; 54-52,096; and 54-157,596; as well as U.K. Patent No. 2,025,933.

However, the process mentioned above must be carried out under severe and complicated reaction conditions, because the process is subject to protection and deprotection of the amino group in the organic acid. This process further suffers from the defect that the acid chloride is unstable.

In another method, 2-pyridinethioester, 2-benzothiazole ester, or 1-hydroxy benzotriazole ester is synthesized from an organic acid of the formula (III):

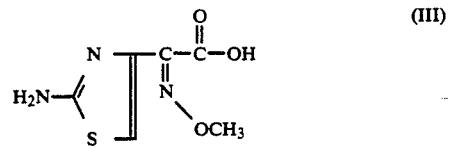

and then the resulting ester is acylated with 7-ADCA, 7-ACA or its derivatives to give a compound of the formula (I): see Japanese Laid-Open (Kokai) Patent Publication No. 52-102,293; 54-95,593; and 56-152,488.

However, this process shows relatively low yields due to a side reaction accompanied when preparing the activated esters. Furthermore the process must be carried out at a high reaction temperature for a long period of reaction time during the acylation step, and requires a step of removing the by-products resulted from the process.

It has also been reported that in order to resolve the problems encountered in utilizing the activated esters, an activated amide solvate of a compound of the formula (III) is isolated from an organic solvent, and then is acylated with 7-ACA or its derivatives to give a compound of the formula (I): see European Patent No. 175,814. However, this process has the disadvantages that it is difficult to isolate the activated amide solvate from the organic solvent used, and that it must be carried out under the substantially similar reaction conditions to those in the cases involving an activated ester or an activated amide, requiring a high reaction temperature and a long period of reaction time.

Meanwhile, T. Fujisawa et al. have reported in Chem. Letters, 1267 (1983) that a lithium carboxylate derivative is reacted with dichlorophosphoran to give a corresponding acyloxyphosphonium salt derivative, and then the resulting acyloxyphosphonium salt is reacted with a Grignard reagent to give a corresponding diketone.

DETAILED DESCRIPTION OF THE INVENTION

Based on the Fujisawa's report, the present inventors have studied a process for preparing β-lactam derivatives of the formula (I), and discovered that an acyloxyphosphonium chloride derivative obtained from an aminothiazole derivative of the organic acid (III) makes it possible that the acylation of 7-ACA or its derivatives with organic acid can be proceeded without the isolation of the acyloxyphosphonium chloride to give the final product, β-lactam derivative, in good purity and high yield. Based on the above discovery, the inventors have now completed the present invention.

Therefore, an object of the present invention is to provide a new process for preparing β-lactam derivative of the formula (I) above, by which the disadvantages of the prior art processes have been eliminated.

Another object of the present invention is to provide a novel process for preparing more economically and simply a compound of the formula (I) above in higher yields and purity as compared with the prior art processes.

According to the present invention, a novel process for preparing a cephem derivative of the formula (I) above, which comprises steps of:

reacting a mixture of triphenylphosphine and hexachloroethane or carbon tetrachloride with an organic acid of the formula (III):

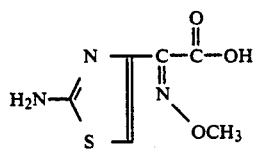

in an organic solvent to give an acyloxyphosphonium chloride derivative of the formula (IV):

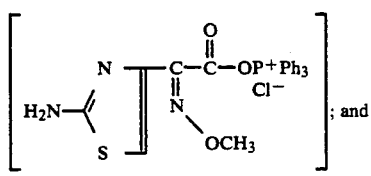

acylating a derivative of 7-ACA of the formula (V):

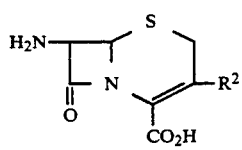

wherein $R^2$ is the same as defined above, which has been previously silylated with a silylating agent in an organic solvent in the presence or absence of a base, with the acyloxyphosphonium chloride derivative without its isolation.

The process of the present invention can be represented by the following reaction scheme:

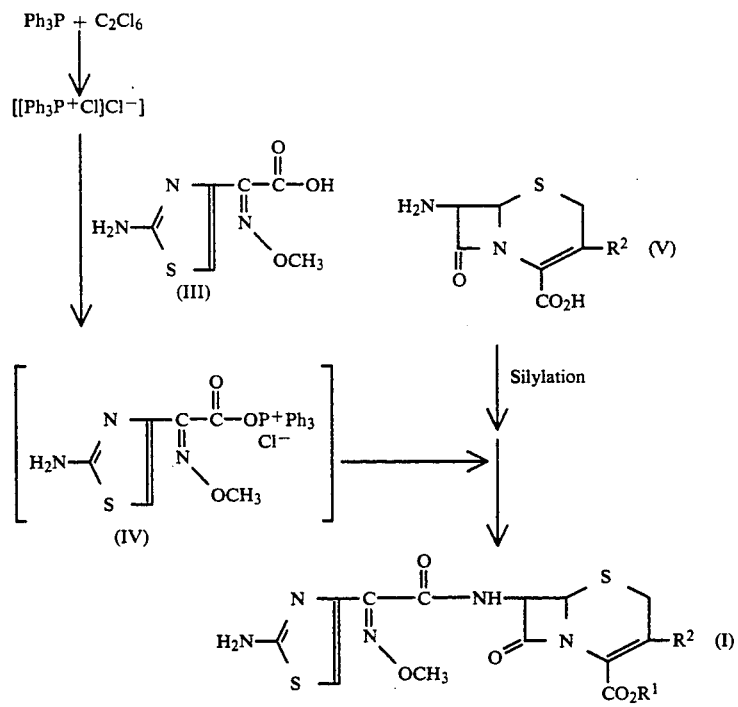

$R^1$ and $R^2$ are the same as defined above.

The acyloxyphosphonium chloride derivative can be synthesized by first reacting triphenylphosphine with hexachloroethane or carbon tetrachloride in an organic solvent to give dichlorophosphoran, which is then reacted with an aminothiazole derivative of the formula (III).

For identifying the acyloxyphosphonium chloride synthesized, a number of attempts to isolate it, such as flash column chromatography and crystallization in a nonpolar solvent, etc., have been made. However, since the acyloxyphosphonium chloride compound is unstable and easily decomposable, its isolation could not be achieved. Thus, the acyloxyphosphonium chloride derivative is synthesized using $CDCl_3$ as a solvent, and then directly sampled followed by identification of its chemical structure by means of the $^1H$-NMR spectra.

The organic solvents for the above reaction may preferably include tetrahydrofuran, dichloromethane, acetonitrile, etc., and most preferably dichloromethane.

Triphenylphosphine and hexachloroethane or carbon tetrachloride are each preferably used in amounts of 1.0–1.3 equivalents to an organic acid of the formula (III).

The reaction for preparing the acyloxyphosphonium chloride is carried out at 0°–30° C. After 0.5–3.0 hours, the acyloxyphosphonium chloride derivative of the formula (IV) is obtained.

The organic solvent for silylation of the compound of the formula (V) may include preferably tetrahydrofuran, dichloromethane, acetonitrile, etc., and most preferably dichloromethane. The silylate agent may include dichlorodimethylsilane, chlorotrimethylsilane, hexamethyldisilazane, and N,O-bis-trimethylsilylacetamide, etc. The silylating agent is used in amounts of 2.0–4.0 equivalents to the compound of the formula (V).

As the base, triethylamine, pyridine and N,N-dimethylaniline, etc. may be preferably used. The silylation reaction is preferably carried out at 10°–45° C. for 0.5–2.0 hours.

The acylation reaction to prepare β-lactam derivatives of the formula (I) is appropriately carried out at between −5° C. to 40° C. for 1–3 hours. This reaction is carried out stoichiometrically. When the reaction is completed, a base such as triethylamine and sodium bicarbonate, and water are added to the reaction mixture, and two layers are then separated. Then, a mixture of organic solvents is added to the aqueous layer, and then the pH of the aqueous layer is adjusted to an isoelectric point to give the final product, β-lactam derivatives of the formula (I), in precipitate form.

PREFERRED EMBODIMENT OF THE INVENTION

The present invention will be described in greater detail by way of the following examples. It should be, however, noted that the examples are presented for illustration purpose only and should not be construed as limiting the invention which is properly delineated in the claims.

EXAMPLE 1

7-[[2-(2-AMINOTHIAZOL-4-YL)-2-SYN-METHOXYIMINO]ACETAMIDO]CEPHALOSPORANIC ACID

Step A

Into a 3-neck flask, 12.14 g of triphenylphosphine, 10.96 g of hexachloroethane and 150.0 ml of dichloromethane were placed. The resulting mixture was stirred for 1 hour at about 20° C. Then, to the mixture, 8.88 g of 2-(2-aminothiazol-4-yl)-2-syn-methoxyiminoacetic acid was added. The resulting mixture was further stirred for 1.5 hours at 20° C. to give a reaction mixture.

Step B

Into a 3-neck flask, 10.0 g of 7-aminocephalosporanic acid, 150.0 ml of dichloromethane and 12.32 g of N,O-bis-trimethylsilylacetamide were added. The resulting mixture was stirred for 1 hour at about 30° C. To the mixture, the reaction mixture obtained from Step A was added dropwise at 20° C. The resulting mixture was stirred for 1 hour. Upon completion of the reaction, 14.0 g of sodium bicarbonate and 180.0 ml of water were added to the reaction mixture which was then stirred to separate a water layer. 90.0 Ml of a mixture solvent of ethyl acetate and n-butanol (8:2) was added to the water layer, which was then adjusted to a pH of about 2.6 to precipitate white crystals. The resulting crystals were filtered out and dried to give 15.02 g (90.0%) of the title compound.

$^1$HNMR (DMSO-d$_6$, δppm): 2.0(s,3H); 3.5(AB,2H); 3.8(s,3H); 4.7(q,2H); 4.8(d,2H); 5.8(dd,1H); 6.8(s,1H); 7.2(s,2H); 9.5(d,1H).

EXAMPLE 2

7-[[2-(2-AMINOTHIAZOL-4-YL)-2-SYN-METHOXYIMINO]ACETAMIDO]CEPHALOSPORANIC ACID

Step A

The same procedure as in Example 1, Step A was repeated to give a reaction mixture.

Step B

Into a 3-neck flask, 10.0 g of 7-aminocephalosporanic acid, 150.0 ml of dichloromethane and 9.28 g of triethylamine were placed. To the mixture, 9.97 g of chlorotrimethylsilane was added dropwise at 15° C. The resulting mixture was stirred for 1.5 hours, to which the reaction mixture obtained from Step A was then added. After stirring for 1 hour at 20° C., 16.0 g of sodium bicarbonate and 200.0 ml of water were added to the mixture which was then stirred again to separate the water layer. 100.0 Ml of a mixture solvent of ethyl acetate and n-butanol (8:2) was added to the water layer, which was then adjusted to a pH of about 2.6 to precipitate white crystals. The resulting crystals were filtered and dried to give 14.55 g (87.2%) of the title compound.

EXAMPLE 3

7-[[2-(2-AMINOTHIAZOL-4-YL)-2-SYN-METHOXYIMINO]ACETAMIDO]CEPHALOSPORANIC ACID

The same procedure as in Example 1 was repeated, except that tetrahydrofuran in the same amount was used in place of dichloromethane. Then, 14.0 g of sodium bicarbonate and 180.0 ml of water were added to the resulting mixture. After the mixture was saturated with NaCl while stirring, the water layer was separated. 90.0 Ml of a mixture solvent of ethyl acetate and n-butanol (8:2) was added to the water layer, which was then adjusted to a pH of about 2.6 to precipitate white crystals. The resulting crystals were filtered out and dried to give 13.97 g (83.7%) of the title compound.

EXAMPLE 4

7-[[2-(2-AMINOTHIAZOL-4-YL)-2-SYN-METHOXYIMINO]-ACETAMIDO]CEPHALOSPORANIC ACID

The same procedure as in Example 1 was repeated, except that acetonitrile in the same amount was used in place of dichloromethane. Then, the resulting mixture were treated in the same manner as described in Example 3 to give 14.10 g (84.5%) of the title compound.

EXAMPLE 5

7-[[2-(2-AMINOTHIAZOL-4-YL)-2-SYN-METHOXYIMINO]ACETAMIDO]CEPHALOSPORANIC ACID

The procedure similar to that described in Example 1 was carried out using 9.77 g of hexamethyldisilazane in place of N,O-bis-trimethylsilyl acetamide. Then, the resulting mixture was treated in the same manner as described in Example 3 to give 14.49 g (86.8%) of the title compound.

EXAMPLE 6

7-[[2-(2-AMINOTHIAZOL-4-YL)-2-SYN-METHOXYIMINO]ACETAMIDO]CEPHALOSPORANIC ACID

Step A

The same procedure as in Example 1 was repeated to give a reaction mixture.

Step B

Into a 3-neck flask, 10.0 g of 7-aminocephalosporanic acid, 150.0 ml of dichloromethane and 9.56 g of N,N-dimethylaniline were placed. To the mixture, 9.47 g of dichlorodimethylsilane was then added dropwise at 15° C. The resulting mixture was stirred for 1.5 hours. To this mixture, the reaction mixture obtained from Step A was added. After stirring at 20° C. for 1 hour, 17.0 g of sodium bicarbonate and 200.0 ml of water were added to the reaction mixture. The mixture was stirred again, and a water layer was separated therefrom. 100.0 Ml of mixture solvent of ethyl acetate and n-butanol (8:2) was added to the water layer, which was then adjusted to a pH of about 2.6 to precipitate white crystals. The resulting crystals were filtered and dried to give 14.35 g (86.0%) of the title compound.

EXAMPLE 7

7-[[2-(2-AMINOTHIAZOL-4-YL)-2-SYN-METHOX-YIMINO]ACETAMIDO1-3-](1-METHYL-1H-TET-RAZOL-5-YL)THIOMETHYL]-3-CEPHEM-4-CARBOXYLIC ACID

Step A

Into a 3-neck flask, 12.14 g of triphenylphosphine, 10.96 g of hexachloroethane and 180.0 ml of dichloromethane were placed. The mixture was stirred for 1 hour at 20° C., to which 8.88 of 2-(2-aminothiazol-4-yl)-2-syn-methoxyimino acetic acid was added. The resulting mixture was stirred for 1.5 hours at 20° C. to give a reaction mixture.

Step B

Into a 3-neck flask, 12.05 g of 7-amino-[3-(1methyl-1H-tetrazol-5-yl) thiomethyl]-3-cephem-4-carboxylic acid, 180.0 ml of dichloromethane and 12.32 g of N,O-bis-trimethylsilyl acetamide were placed. The mixture was stirred for 1 hour at 30° C. To the mixture, was added dropwise the reaction mixture obtained from Step A at 20° C. The resulting mixture was then stirred for 1.5 hours. After completion of the reaction, 13.0 g of sodium bicarbonate and 180.0 ml of water were added to the reaction mixture. After the mixture was stirred, the water layer was separated. 95.0 Ml of a mixture solvent of ethyl acetate and n-butanol (8:2) was added to the water layer, which was then adjusted to a pH of about 2.8 to precipitate crystals. The resulting crystals were filtered out and dried to give 16.60 g (88.4%) of the title compound.

$^1$HNMR (D$_2$O/NaHCO$_3$,δppm): 3.84(d,2H); 4.01(s,3H); 4.05(s,3H); 5.18(d,1H); 5.76(d,1H); 7.00(s,1H).

EXAMPLE 8

7-[[2-(2-AMINOTHIAZOL-4-YL)-2-SYN-METHOX-YIMINO]ACETAMIDO]-3-[(1-METHYL-1H-TET-RAZOL-5-YL)THIOMETHYL]3-CEPHEM-4-CARBOXYLIC ACID

The same procedure as in Example 7 was repeated, except that acetonitrile in the same amount was used in place of dichloromethane. Then, 13.0 g of sodium bicarbonate and 170.0 ml of water were added to the resulting reaction mixture. After the reaction mixture was saturated with NaCl while stirring, a water layer was separated by extracting with 150 ml of dichloromethane. 80.0 Ml of a mixture solvent of ethyl acetate and n-butanol (8:2) was added to the water layer which was then adjusted to a pH of about 2.8 to precipitate crystals. The resulting crystals were filtered out and dried to give 15.90 g(84.7%) of the title compound.

EXAMPLE 9

7-[[2-(2-AMINOTHIAZOL-4-YL)-2-SYN-METHOX-YIMINO]ACETAMIDO]-3-CEPHEM-4-CARBOXYLIC ACID

Step A

Into a 3-neck flask, 12.14 g of triphenylphosphine, 10.96 g of hexachloroethane and 170 0 ml of dichloromethane were placed. The mixture was stirred for 1 hour at about 20° C., to which 8.88 g of 2-(2-aminothiazol-4-yl)-2-syn-methoxyimino acetic acid was added. The mixture was stirred for 1.5 hours at 20° C. to give a reaction mixture.

Step B

Into a 3-neck flask, 7.35 g of 7-amino-3-cephem-4carboxylic acid, 170.0 ml of dichloromethane and 7.84 g of pyridine were placed. To the mixture, 11.84 g of dichlorodimethylsilane was added dropwise at 10° C. The resulting mixture was stirred for 1.5 hours at 20° C. To this mixture, the reaction mixture obtained from Step A was added, and then the resulting mixture was stirred for 1.5 hours at 10° C. After completion of the reaction, 16.5 g of sodium bicarbonate and 210.0 ml of water were added to the mixture. The mixture was stirred, and then a water layer was separated. 100.0 Ml of mixture solvent of ethyl acetate and n-butanol (8:2) was added to the water layer, which was then adjusted to a pH of about 2.9 to precipitate crystals. The resulting crystals were filtered out and dried to give 12.61 g (89.6%) of the title compound.

$^1$HNMR (DMSO-d$_6$,δppm): 3.58(bs,2H); 3.84(s,3H); 5.12(d,1H); 5.84(d,1H); 6.51(s,1H); 6.77(s,1H); 7.26(bs,2H); 9.65(d,1H).

EXAMPLE 10

7-[[2-(2-AMINOTHIAZOL-4-YL)-2-SYN-METHOX-YIMINO]OXO-AS-TRIAZIN-3YL) THIOMETHYL]-3-CEPHEM-4-CARBOXYLIC ACID

Step A

Into a 3-neck flask, 12.14 g of triphenylphosphine, 10.96 g of hexachloroethane and 150.0 ml of dichloromethane were placed. The mixture was stirred for hour at about 20° C., to which 8.88 g of 2-(2-aminothiazol-4-yl)-2-syn-methoxyimino acetic acid was added. The mixture was stirred for 1.5 hours at 20° C. to give a reaction mixture.

Step B

Into a 3-neck flask, 13.62 g of 7-[amino-3-(2,5- dihydro-2-methyl-6-hydroxy-5-oxo-as-triazin-3-yl)thiomethyl]-3-cephem-4-carboxylic acid, 200 ml of dichloromethane and 26.13 g of N,O-bis-trimethylsilylacetamide were placed. The mixture was stirred for hour at about 30° C. To the resulting mixture, was added dropwise the reaction mixture obtained from Step A at 10° C. The resulting mixture was then stirred for 1 hour. After completion of the reaction, 16.0 g of sodium bicarbonate and 180.0 ml of water were added to the reaction mixture. After the mixture was stirred, the water layer was separated. 50.0 Ml of a mixture solvent of ethyl acetate and n-butanol (8:2) was added to the water layer adjusted to a pH of about 3.1 to precipitate crystals. The resulting crystals were filtered out and dried to give 18.45 g (90.6%) of the title compound.

$^1$HNMR (DMSO-d$_6$,δppm): 3.2(d,2H); 3.61(s,3H); 3.95(s,3H); 4.21(d,2H); 5.18(d,1H); 5.72(d,1H); 6.95(s,1H); 7.2(bs,2H); 9.45(d,1H).

EXAMPLE 11

7-[[2-(2-AMINOTHIAZOL-4-YL)-2-SYN-METHOX-YIMINO]ACETAMIDO]3-[(2,5-DIHYDRO-6-HYDROXY-2-METHYL-5-OXO-AS-TRIAZIN-3-YL)THIOMETHYL]-3-CEPHEM-4-CARBOXYLIC ACID

The same procedure as in Example 10 was repeated, except that acetonitrile in the same amount was used in place of dichloromethane. Then, the resulting reaction mixture was treated in the same manner as described in Example 3 and adjusted to a pH of about 3.1 to precipitate crystals. The resulting crystals were filtered out and dried to give 17.53 g (86.1%) of the title compound.

EXAMPLE 12

7-[[2-(2-AMINOTHIAZOL-4-YL)-2-SYN-METHOXYIMINO]ACETAMIDO]3-](2,5-DIHYDRO-6-HYDROXY -2-METHYL-5-OXO-AS-TRIAZIN-3-YL)THIOMETHYL]-3-CEPHEM-4-CARBOXYLIC ACID

Step A

The same procedure as in Example 10 was repeated to give a reaction mixture.

Step B

Into a 3-neck flask, 13.62 g of 7-[amino-3-(2,5- dihydro-2-methyl-6-hydroxy-5-oxo-as-triazin-3yl)thiomethyl]3-cephem-4-carboxylic acid, 200.0 ml of dichloromethane and 14.84 g of triethylamine were placed. To the mixture, 16.58 g of dichlorodimethylsilane was added dropwise at 15° C. The resulting mixture was stirred for 1 hour, to which the reaction mixture obtained from Step A was then added, and the resulting mixture was stirred for 1 hour at 10° C. After completion of the reaction, 17.0 g of sodium bicarbonate and 210.0 ml of water were added to the reaction mixture. After the mixture was stirred, the water layer was separated. 100.0 Ml of a mixture solvent of ethyl acetate and n-butanol (8:2) was added to the water layer, which was then adjusted to a pH of about 3.1 to precipitate crystals. The resulting crystals were filtered out and dried to give 17.30 g (85.0%) of the title compound.

EXAMPLE 13

7-[[2-(2-AMINOTHIAZOL-4-YL)-2-SYN-METHOXYIMINO]ACETAMIDO]CEPHALOSPORANIC ACID

The same procedure as in Example 1 was repeated, except that carbon tetrachloride in the same equivalent was used in place of hexachloroethane. Then, the resulting reaction mixture was treated in the same manner as described in Example 1 to give 14.67 g (87.9%) of the title compound.

EXAMPLE 14

7-[[2-(2-AMINOTHIAZOL-4-YL)-2-SYN-METHOXYIMINO]ACETAMIDO]3-](2,5-DIHYDRO-6-HYDROXY -2-METHYL-5-OXO-AS-TRIAZIN-3-YL)THIOMETHYL]-3-CEPHEM-4-CARBOXYLIC ACID

The same procedure as in Example 10 was repeated, except that carbon tetrachloride in the same equivalent was used in place of hexachloroethane. Then, the resulting reaction mixture was treated in the same manner as described in Example 10 to give 17.8 g (87.4%) of the title compound.

As described above, the present invention is featured by removing the steps of protecting and deprotecting the amino group in the aminothiazole derivative (III). Also, the subsequent acylation step can be carried out without isolation of the acyloxyphosphonium chloride of the formula (IV). Furthermore, the reactions involved may be carried out at near room temperature in a relatively short reaction time.

In addition to the advantages mentioned above, after the completion of the reactions involved, the separation of the desired product can be easily achieved by adding a mixture of organic solvents to the aqueous layer. Thus, according to the present invention β-lactam derivatives, which are a useful antibiotic, of the formula (I) above and prepared more economically and simply in high yields and purity.

What is claimed is:

1. A process for preparing a compound of the formula:

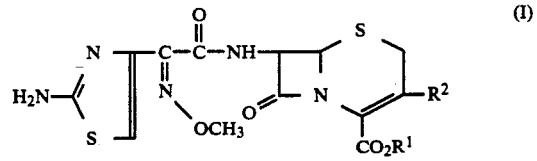

wherein $R^1$ represents hydrogen or a metal salt; and $R^2$ represents hydrogen, acetoxymethyl, (1-methyl-1H-tetrazol-5-yl)thiomethyl or (2,5-dihydro-2-methyl-6-hydroxy-5-oxo-as-triazin-3-yl)thiomethyl, which process comprises the steps of:

(a) reacting a mixture of triphenylphosphine (Ph₃P) and hexachloroethane ($C_2Cl_6$) or carbon tetrachloride ($CCl_4$) with an organic acid of the formula:

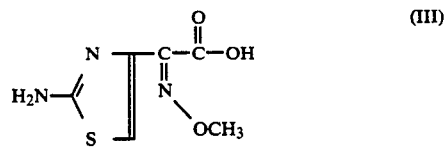

in an organic solvent to give an acyloxyphosphonium chloride derivative of the formula:

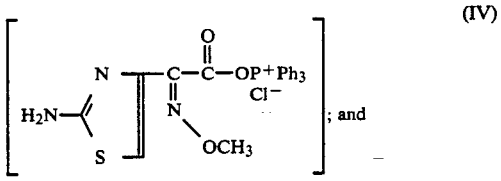

(b) acylating a silylated derivative of 7-ACA of the formula (V):

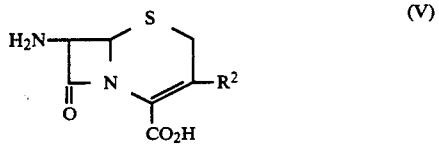

wherein $R^2$ is the same as defined above, wherein the acyloxyphosphonium chloride derivative is not isolated.

2. The process of claim 1, wherein the organic solvent is selected from the group consisting of dichloromethane, acetonitrile and tetrahydrofuran.

3. The process of claim 1, wherein the silylated derivative is prepared by silylating 7-ACA or its derivative with a silylating agent selected from the group consisting of dichlorodimethylsilane, chlorotrimethylsilane, hexamethyldisilazane and N,O-bis-trimethylsilylacetamide in an organic solvent in the presence or absence of a base.

4. The process of claim 3, wherein the base is selected from the group consisting of triethylamine, pyridine and N,N-dimethylaniline.

5. The process of claim 1, wherein the acylation reaction is carried out for 1 to 3 hours at −5° C. to 40° C.

6. The process of claim 1, wherein triphenylphosphine, hexachloroethane or carbon tetrachloride is used in the amounts of 1.0 to 1.3 equivalents to the organic acid of the formula (III).

* * * * *